US011458277B2

(12) United States Patent
Takehara et al.

(10) Patent No.: US 11,458,277 B2
(45) Date of Patent: Oct. 4, 2022

(54) BIOACTIVATION METHOD FOR ENHANCING NEURAL ACTIVITY AND BLOOD CIRCULATION ACTIVITY OF LIVING BODY

(71) Applicant: Aqua Bank CO., LTD., Osaka (JP)

(72) Inventors: Takashi Takehara, Osaka (JP); Yukihiro Yada, Osaka (JP)

(73) Assignee: AQUA BANK CO., LTD, Osaka (JP)

( * ) Notice: Subject to any disclaimer, the term of this patent is extended or adjusted under 35 U.S.C. 154(b) by 348 days.

(21) Appl. No.: 16/482,881

(22) PCT Filed: Feb. 13, 2018

(86) PCT No.: PCT/JP2018/004919
§ 371 (c)(1),
(2) Date: Aug. 1, 2019

(87) PCT Pub. No.: WO2018/151107
PCT Pub. Date: Aug. 23, 2018

(65) Prior Publication Data
US 2020/0121884 A1 Apr. 23, 2020

(30) Foreign Application Priority Data
Feb. 14, 2017 (JP) .............................. JP2017-025450

(51) Int. Cl.
*A61M 16/12* (2006.01)
*A61K 33/00* (2006.01)
(Continued)

(52) U.S. Cl.
CPC ............. *A61M 16/12* (2013.01); *A61K 33/00* (2013.01); *C25B 1/04* (2013.01); *C25B 9/17* (2021.01);
(Continued)

(58) Field of Classification Search
CPC .......... A61M 15/06; C25B 1/04; Y02E 60/36; A24F 40/10; A24F 47/002; A24F 40/05; C01B 11/024
See application file for complete search history.

(56) References Cited

U.S. PATENT DOCUMENTS

2009/0035383 A1 2/2009 Murota
2010/0291228 A1 11/2010 Ohta et al.
(Continued)

FOREIGN PATENT DOCUMENTS

| CN | 104379812 A | 2/2015 |
|---|---|---|
| JP | 2004-041949 A | 2/2004 |

(Continued)

*Primary Examiner* — Margaret M Luarca
(74) *Attorney, Agent, or Firm* — Novick, Kim & Lee, PLLC; Jae Youn Kim

(57) ABSTRACT

Provided are a bioactivation method for enhancing a neural activity and/or a blood circulation activity of a living body and a hydrogen generating device for executing this method. In the method, a gas mixture containing hydrogen and oxygen at predetermined concentrations is suctioned by spontaneous breathing continuously for a predetermined time. Moreover, this hydrogen generating device for executing the bioactivation method for enhancing a neural activity and/or a blood circulation activity of a living body includes a body cover member including a battery, a control substrate for controlling power supply from the battery, and a pair of positive/negative electrodes electrically conducted with or shut down from a positive electrode and a negative electrode of the battery by the control substrate.

4 Claims, 10 Drawing Sheets

(51) Int. Cl.
  *C25B 1/04* (2021.01)
  *C25B 9/17* (2021.01)
(52) U.S. Cl.
  CPC . *A61M 2202/02* (2013.01); *A61M 2202/0208* (2013.01)

(56) References Cited

U.S. PATENT DOCUMENTS

| | | |
|---|---|---|
| 2013/0177653 A1 | 7/2013 | Ohta |
| 2018/0209050 A1* | 7/2018 | Tak ......................... C02F 1/725 |
| 2019/0015446 A1* | 1/2019 | Suzuki ................... A61P 25/28 |

FOREIGN PATENT DOCUMENTS

| | | |
|---|---|---|
| JP | 2014-019640 A | 2/2014 |
| JP | 2016-073583 A | 5/2016 |
| JP | 2017012501 A | 1/2017 |
| WO | 2007/021034 A1 | 2/2007 |

* cited by examiner

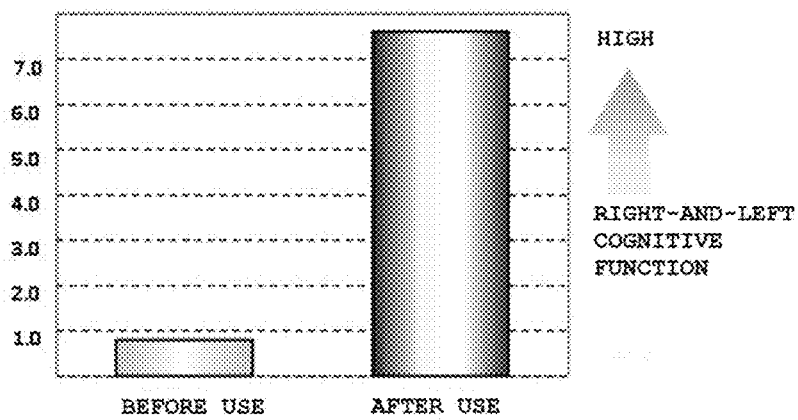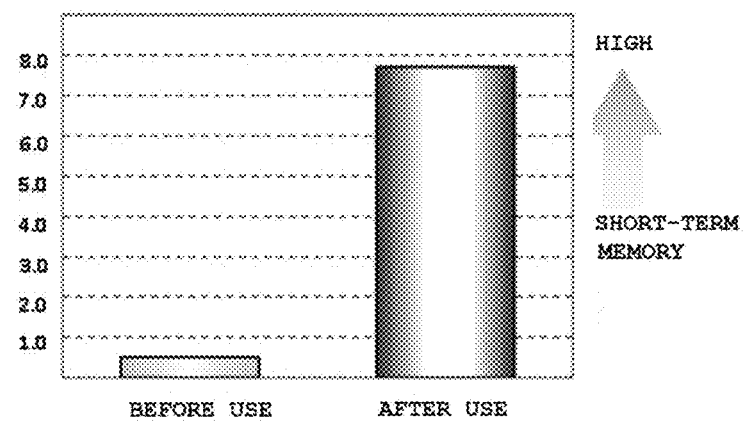
FIG. 5

BIOACTIVATION METHOD FOR ENHANCING NEURAL ACTIVITY AND BLOOD CIRCULATION ACTIVITY OF LIVING BODY

TECHNICAL FIELD

The present invention relates to a bioactivation method for enhancing a neural activity and/or a blood circulation activity of a living body by suctioning hydrogen at a predetermined concentration for a predetermined time and a hydrogen generating device for executing this method.

BACKGROUND ART

Recently, effectiveness of hydrogen has attracted attention in various animal disease experiments such as neurodegenerative diseases and acute lung disorders and human clinical tests for metabolic syndrome, diabetes and the like, and various studies have been actively conducted in medical applications. Hydrogen is said to be effective to remove only malignant active oxygens (=hydroxyl radical) accelerating aging and causing various diseases such as arteriosclerosis and cancers from an inside of the body, and since it does not badly affect tissues and cells in the body, it has a wide variety of methods for taking into the body such as intravenous dosage, oral administration of aqueous solution, and gas inhalation.

Intake of hydrogen into the body is recommended particularly for preventing aging or for promoting beauty/health in various states during physical exercises, eating and drinking, smoking, stay under ultraviolet/contaminated environments, and under a high stress such as lack of sleep and long-hour work, in which active oxygen tends to be generated easily in the body.

However, medical trial cases have been found mainly in administration of an aqueous solution containing hydrogen, instillation and the like, and definite trials have not been conventionally provided for gas suctioning. Moreover, the objects of the trial cases are effects for days or years after intake of hydrogen, and there have been no trial results paying attention to an immediate effect or the effect in short time to mind and body.

Moreover, in view of pseudo electronic cigarettes in the recent non-smoking boom or an expansion of the market for cigarettes not emitting sidestream smoke, hidden needs for smoking hydrogen leading to health promotion is considered to be large. On the other hand, such a concern is pointed out that the market relies on speculation/emotion of the effect of the hydrogen suctioning to mind and body. Therefore, the necessity of trial cases on what vital reactions are actually caused by intake of hydrogen is in demand.

Furthermore, there are roughly two methods as a hydrogen generating method, that is, the one using a hydrogen generating chemical reaction such as chemical reaction between magnesium particles, aluminum particles or the like and water as in Patent Literature 1, for example, and an electrolysis method of water as in Patent Literature 2, for example, and when the aforementioned trial cases are provided, provision of specific configuration for a desired amount of hydrogen to be taken within a desired time in accordance with that is also required.

CITATION LIST

Patent Literature

Patent Literature 1: Japanese Patent Laid-Open No. 2004-41949
Patent Literature 2: Japanese Patent Laid-Open No. 2014-019640

SUMMARY OF INVENTION

Technical Problem

The present invention was made in view of the aforementioned circumstances and has an object to provide a bioactivation method for enhancing a neural activity and/or a blood circulation activity of a living body which can quickly generate psychological/physiological effects such as favorable brain activation by suctioning a hydrogen gas at a predetermined concentration continuously for a predetermined time.

Moreover, the present invention has an object to specifically provide a hydrogen generating device which enables a user to suction the hydrogen gas easily, not depending on time or place for executing this method for activation of a living body.

Solution to Problem

In order to solve the aforementioned problems, in a bioactivation method for enhancing a neural activity and/or a blood circulation activity of a living body of the present invention, a gas mixture containing hydrogen and oxygen at predetermined concentrations by spontaneous breathing is suctioned continuously for a predetermined time.

More specifically, a normal air by spontaneous breathing and the gas mixture emitted from the hydrogen generating device which electrolyzes water are mixed with the normal air under spontaneous breathing, and the same degree of the oxygen concentration as that of the normal air is suctioned orally and the like.

In more detail, the suctioning is preferably performed for approximately 10 minutes under spontaneous breathing.

By executing the method of the present invention of orally suctioning the hydrogen gas at the predetermined concentration continuously for the predetermined time, favorable psychological/physiological effects can be quickly generated as is obvious from trial cases which will be described later. It is particularly marked in brain activation. According to the present invention, provision of a specific intake method/favorable psychological/physiological effects in hydrogen intake into a living body is largely advantageous. In more detail, it is recommended that hydrogen and oxygen are generated by electrolyzing water, and they are orally suctioned for approximately 10 minutes with environmental air while exercising spontaneous breathing. By using the electrolysis, a favorable hydrogen amount can be taken from the pulmonary artery in accordance with a power supply amount. At the same time, a bioeffect of only hydrogen excluding the bioeffect of oxygen can be given to a human body in correlation with concentrations of oxygen and hydrogen in the environmental air (oxygen is largely contained under the environmental air), which is also advantageous.

Moreover, the present invention specifically provides a suitable hydrogen generating device so that the activation method for a living body for enhancing the neural activity and/or the blood circulation activity of a living body of the present invention is specifically executed and an ordinary user can take in hydrogen when the user wants a desired bioeffect.

In more detail, this hydrogen generating device preferably includes:

a body cover member including a battery, a control substrate for controlling power supply from the battery, and a pair of positive/negative electrodes electrically conducted with or shut down from a positive electrode and a negative electrode of the battery by the control substrate;

an electrolysis tank capable of storing water and detachably mounted on the body cover member and into which the pair of positive/negative electrodes are inserted therein in the mounted state;

a nozzle portion having a through hole; and a mixing portion fluidically connecting the nozzle portion and an end portion of the electrolysis tank and having a channel for taking in the environmental air.

This hydrogen generating device is a portable device utilizing the electrolysis as described above, and hydrogen can be taken orally not depending on the place/environment, and the user can obtain the desired psychological/physiological effects in a short time.

According to this hydrogen generating device, since this is a charging type so that the user can carry it freely, the battery is small-sized and inexpensive but a space for storing the battery and water shielding between the electrolysis tank and the battery are ensured and moreover, a sufficient amount of hydrogen gas generated can be ensured even if it is tilted in a state where the water in the electrolysis tank has decreased, hydrogen can be suctioned so as to obtain the aforementioned psychological/physiological effects easily and in a short time as the user wishes, not depending on the place.

Advantageous Effect of Invention

According to the bioactivation method for enhancing the neural activity and/or blood circulation activity of a living body and the hydrogen generating device for executing this method of the present invention, the psychological/physiological effects such as brain activation can be generated quickly and favorably by suctioning the hydrogen gas at the predetermined concentration continuously for the predetermined time and moreover, the user can suction the hydrogen gas easily not depending on the place or time.

BRIEF DESCRIPTION OF DRAWINGS

FIG. 5 illustrates a graph illustrating an average before and after the suctioning of hydrogen by the subject in evaluation of short-term memory and right-and-left cognitive function.

FIGS. 8(a), 8(b), 8(c), 8(d) and 8(e) are views of the electrolytic hydrogen gas suction tool in FIG. 7 seen from each direction, in which FIG. 8(a) is a left side view, FIG. 8(b) is a front view, FIG. 8(c) is a right side view, FIG. 8(d) is a bottom view, and FIG. 8(e) is a top view.

DESCRIPTION OF EMBODIMENT

Figure 1:
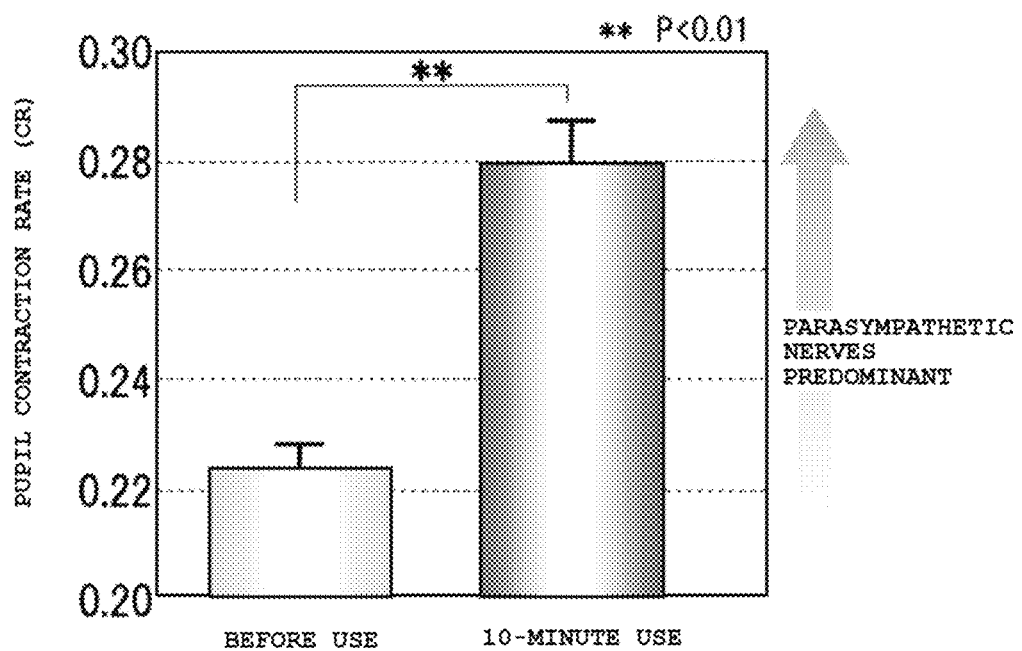
FIG. 1 illustrates a measurement graph illustrating a pupil contraction rate (CR value) of an average of right and left eyes of a subject shown before and after suctioning of hydrogen.

Hereinafter, a bioactivation method for enhancing a neural activity and/or a blood circulation activity of a living body of the present invention will be exemplified, and verification test results of psychological/physiological effects thereof will be described.

This method has an object of enhancing the neural activity and/or the blood circulation activity by orally suctioning hydrogen as described above, and the verification tests thereof are for confirming that a parasympathetic system becomes predominant by orally suctioning hydrogen or the like, and fatigue is reduced by a physiological index and also for confirming time until the physiological index is changed.

In the verification test using this method, hydrogen mainly produced by the hydrogen generating device (an electrolytic hydrogen gas suction tool 100 which will be described later) is orally suctioned. More specifically, hydrogen generated by the hydrogen generating or device 100 is suctioned by spontaneous breathing for approximately 10 minutes. The amount of hydrogen generated per minute is 8 cc per minute by electrolysis (4 cc of oxygen is also generated at the same time) and thus, 12 cc per minute of a gas mixture of oxygen/hydrogen is generated. This gas mixture is suctioned by spontaneous breathing. Normally, since an adult suctions approximately 5 litters of air per minute under spontaneous breathing, assuming that all the generated gas mixture is suctioned, the gas mixture at 0.24% at the maximum (hydrogen 0.18%, oxygen 0.06%) is contained in an expiratory air.

The gases generated from the hydrogen generating device 100 are hydrogen and oxygen, and the hydrogen concentration and the oxygen concentration both increase in the gas mixture than the atmosphere, but each of an increase in the concentration is 0.18% for hydrogen and 0.06% in oxygen, and each concentration in the atmosphere is $0.5 \times 10^{-4}\%$ (=0.5 ppm) for hydrogen and approximately 21% for oxygen. Therefore, the oxygen concentration rarely increases in the gas mixture, but only the hydrogen concentration is considered to increase.

The subjects were 20 selected subjects, grouped into two groups, considering the ages and test time slots (morning and afternoon), and measurement was conducted for 10 subjects a day. The selected subjects were healthy women in their 20's to 30's, and the following were excluded: (1) those who have smoking habit; (2) those who are sensitive to cold (including those who feel cold in hands and feed even in summer); (3) those who currently have some disease and undergo medical treatment; (4) those who have taken drugs or habitual drug application for the purpose of disease treatment in the past one month (cold is excluded, treatment history for pollinosis is included); (5) those who have past history or present illness of serious disorder in lever, kidney, heart, lung, blood and the like; (6) those who have hypertension symptoms such as systolic pressure of 160 mmHg or more or diastolic pressure of 100 mmHg or more; (7) those who have donated blood exceeding 200 mL in the past one month or 400 mL within three months; (8) those who are pregnant, breast feeding or have a chance to be pregnant; (9) those who have dermatosis symptoms such as atopic dermatitis; (10) those who had surgical operations in a test portion in the past six months; (11) those who are currently participating in the other human clinical tests or one month has not elapsed after participation in the other human clinical tests; and (12) any others who are determined by staff in charge of research to be inappropriate as a target of this test.

Moreover, the subjects were given instructions before participating in the test that (1) they should take sufficient sleep (approximately 7 hours) in the previous day; (2) they should not take stimulus food such as curry and Korean pickles in the food, caffeine drinks such as coffee and tea before the test; (3) they should not put on cosmetics with scent such as fragrance and perfume on the day of measurement (scent-free cosmetic is allowed); (4) they should accept that they should take off their makeups and have the face without makeup for measurement on the day of measurement; and (5) glasses and contact lenses should be taken off for measurement on the day of the test (which may be before the measurement).

The testing method is as follows:
(1) In the main test, each subject should suction hydrogen.
(2) Tests/evaluations which will be described later shall be conducted for each subject while each subject is suctioning hydrogen, and by comparing/examining each evaluation before and after the suctioning, physiological effects by hydrogen is verified.
(3) For the subject who is sitting on a chair for measurement with his/her eyes open, a test manager or a test cooperator prepares a hydrogen generating tool (not generating hydrogen) which is a control and assigns it to the subject. The subject shall put his/her mouth to a nozzle 5 of an electrolytic hydrogen gas suction tool 100 which is this hydrogen generating device (see FIGS. 7 to 10) or a tube portion connected to that and normally breath for approximately 10 minutes. After that, each measurement which will be described later is conducted at any time. After that, the subject puts his/her mouth to the nozzle 5 of the electrolytic hydrogen gas suction tool 100 which generates hydrogen or the tube portion connected to that as a subject sample and suctions hydrogen for 10 minutes similarly. After that, each measurement is made. If abnormality is found in the subject while the subject is suctioning hydrogen, the test manager or the test cooperator shall immediately stop the suctioning. When the suctioning of hydrogen is stopped, the practitioner shall record the fact of the stop and suctioning time in a clinical report.
(4) The test manager shall check if a harmful phenomenon has occurred in the subject during the test or not.

In this verification test of the bioactivation method for enhancing a neural activity and/or a blood circulation activity of a living body, specifically, the following tests were conducted and evaluated:
1) Measurement of Autonomous Nervous System For analysis of an action of the autonomous nervous system, a method of measuring pupil reaction to light and a method of measuring skin temperature of a palm part (index finger) which is highly sensitive but applies a small burden on the subject and can accomplish measurement in a short time are conducted. The measurement methods will be described below.

1-1) Pupil Reflection to Light

After a measuring tool for goggles for measuring a pupil diameter is attached, when the subject is used to a night vision (usually, in the night-vision state for 2 minutes), by irradiating a light emission diode light in extremely weak red color to a pupil portion in a short time such as 0.2 to 1.0 seconds, such a reaction that the pupil is transitorily contracted by light reflex and then, the pupil quickly expands. Thus, a change in the pupil diameter during the pupil contraction/pupil dilatation reaction during this time before and after the operation is photographed by a highly sensitive CCD camera (measurement instrument: iriscorder by Hamamatsu Photonics K.K.), and by analyzing the change in the pupil diameter, a pupil contracting speed and a pupil expanding speed, it is determined whether the sympathetic nervous activity is more predominant or the parasympathetic nervous activity is more predominant in the autonomous nervous activity. If the parasympathetic nervous activity is predominant, the pupil diameter becomes smaller when the light is sensed, the pupil contraction rate (CR) becomes larger and thus, the larger the pupil contraction rate (CR) is, the more predominant the parasympathetic nervous activity is.

1-2) Fingertip Temperature

By paying attention to a physiological reaction that a skin temperature of a distal end section (the forehead center part and a first knuckle-joint cushion side part of the index finger are measured this time) is changed in accordance with predominance of the sympathetic nervous activity, the change in the skin temperature is measured by a temperature sensor over time before and after drinking of the hydrogen solution. The temperature sensor body has an approximate size of a thickness of 1 mm and a diameter of 3 mm, and the change in the skin temperature is measured by a recorder in a wired manner from the sensor.

2) Measurement of Central Nervous System

For an action of the central nervous activity by hydrogen, a brain stress test utilized for the purpose of evaluating an activity degree and a stress degree of the brain is conducted, and the brain activity degree (degree of fatigue) is measured by a flicker device. Moreover, influences of a sight function, a skin sensibility function, a gravity balance function and the like are measured by a brain executive function meter. For a change in emotional feelings, an ability of concentration, sleepiness and the like are examined by interview by using a multilateral emotional state scale. The respective measurements will be described in brief below.

2-1) Brain Stress Test

The brain stress and a rotation degree of the brain (activity degree) are evaluated and analyzed by conducting a test in which number-letter-number-letter (1→A→2→B → 3→C . . . T→20) displayed on a monitor screen are touched in order. This measurement is made immediately after the control and the subject sample (hydrogen) are suctioned.

2-2) Flicker Measurement

The brain activity degree (can be also regarded as a degree of fatigue) is measured by determining a frequency (flicker value) at which green LED light whose frequency changes from 70 to 30 Hz is flashed. More specifically, the frequency is determined when the frequency is continuously decreased from 70 Hz is sensed to be changed to flashing in green. This measurement is repeated 5 times. This measurement is made immediately after the control and the subject sample (hydrogen) are suctioned.

2-3) Brain Function Measurement

Actions to the brain executive functions (right-and-left cognitive function, sight function, short-time memory, skin sensibility, gravity balance and the like are comprehensively analyzed (measurement instrument: Brain executive function meter by Anima). More specifically, tests in which it is determined which of right and left of the center line a white circle on a personal computer is located, and a button is pushed as soon as possible and in which it is determined which of right and left vibration plates is to vibrate as soon as possible, and a button is pushed or measurement of a gravity-center moving distance while standing upright for 30 seconds on a body sway meter and the like are conducted. This measurement is made immediately after the control and the subject sample (hydrogen) are suctioned.

2-4) Multilateral Emotional State Scale

Four subscales and twenty items of "depression/anxiety", "boredom", "active comfortableness", and "non-active comfortableness" were used. Subjective evaluation is made in five-grade evaluation from "not felt at all=0" to "clearly felt=4" immediately after the control and the subject sample (hydrogen) are suctioned.

The aforementioned test results will be described.

The result of the pupil reflection to light in 1-1) is as in the following Table 1, and FIG. 1 shows a measurement graph illustrating an average pupil contraction rate (CR value) of right and left eyes of the 17 subjects excluding those inappropriate from the subjects before and after suctioning of hydrogen. It was confirmed from this Table 1 and FIG. 1 that the pupil contraction rate (CR value) was significantly increased by hydrogen suctioning, and the parasympathetic nervous activity became predominant. This result can be considered to suggest a sedative effect by the hydrogen suctioning.

TABLE 1

| | CR value (right eye) | | | CR value (left eye) | | |
|---|---|---|---|---|---|---|
| Subject | Before | After | Difference | Before | After | Difference |
| 1 | 0.20 | 0.21 | +0.01 | 0.27 | 0.29 | +0.02 |
| 2 | 0.16 | 0.20 | +0.04 | 0.16 | 0.16 | ±0.00 |
| 3 | 0.03 | 0.03 | ±0.00 | 0.07 | 0.08 | +0.01 |
| 4 | 0.22 | 0.30 | +0.08 | 0.24 | 0.32 | +0.08 |
| 5 | 0.24 | 0.23 | −0.01 | 0.24 | 0.22 | −0.02 |
| 6 | 0.24 | 0.41 | +0.17 | 0.24 | 0.38 | +0.14 |
| 7 | 0.36 | 0.38 | +0.02 | 0.34 | 0.38 | +0.04 |
| 9 | 0.22 | 0.30 | +0.08 | 0.20 | 0.32 | +0.12 |
| 11 | 0.13 | 0.18 | +0.05 | 0.13 | 0.18 | +0.05 |
| 12 | 0.23 | 0.30 | +0.07 | 0.25 | 0.30 | +0.05 |
| 13 | 0.39 | 0.41 | +0.02 | 0.39 | 0.41 | +0.02 |
| 14 | 0.19 | 0.45 | +0.26 | 0.21 | 0.30 | +0.09 |
| 16 | 0.16 | 0.24 | +0.08 | 0.17 | 0.21 | +0.04 |
| 17 | 0.13 | 0.28 | +0.15 | 0.14 | 0.29 | +0.15 |
| 18 | 0.50 | 0.36 | −0.14 | 0.42 | 0.34 | −0.08 |

TABLE 1-continued

| | CR value (right eye) | | | CR value (left eye) | | |
|---|---|---|---|---|---|---|
| Subject | Before | After | Difference | Before | After | Difference |
| 20 | 0.21 | 0.18 | −0.03 | 0.19 | 0.17 | −0.02 |
| 21 | 0.40 | 0.30 | −0.10 | 0.29 | 0.29 | ±0.00 |
| Ave. | 0.23 | 0.28 | +0.04 | 0.23 | 0.27 | +0.04 |

Figure 2:
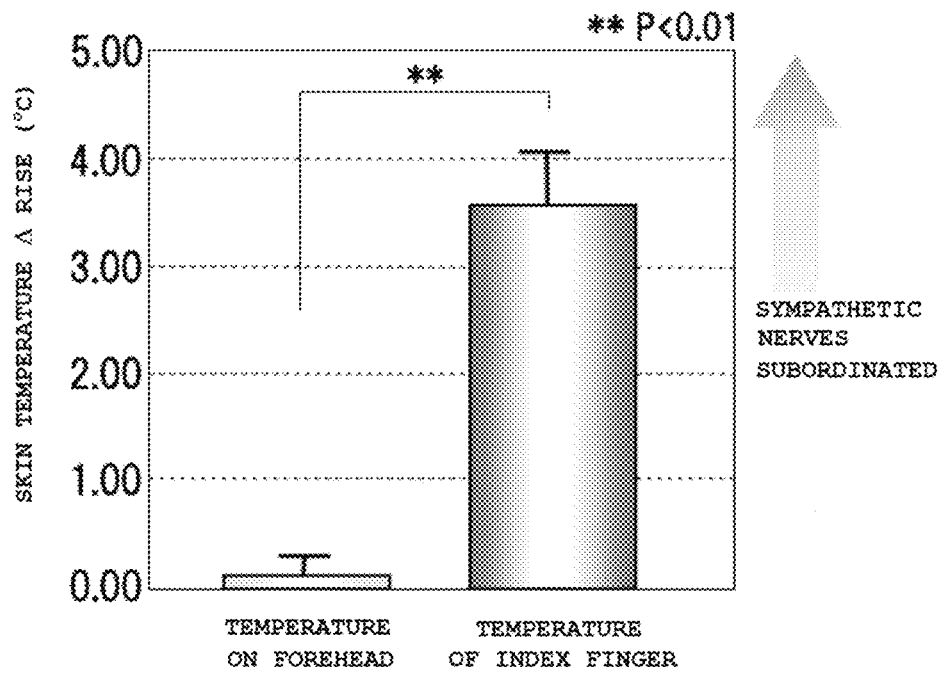
FIG. 2 illustrates a measurement graph illustrating a rising temperature (° C.) of the skin on the index finger before and after the suctioning of hydrogen of the subject and the rising temperature (° C.) of the forehead skin measured separately before and after the suctioning of hydrogen.

The result of 1-2) Fingertip temperature is as in the following Table 2, and FIG. 2 shows a measurement graph illustrating the temperature rise (° C.) of the index finger skin and separately measured temperature rise (° C.) of the forehead skin of the 17 subjects before and after the hydrogen suctioning similarly to FIG. 1. It was suggested from this Table 2 and FIG. 2 that peripheral skin temperature was significantly raised by hydrogen suctioning, the sympathetic nervous activity was suppressed, and the parasympathetic nervous activity became predominant.

TABLE 2

| | Fingertip temperature | | |
|---|---|---|---|
| Subject | Before | After | Difference |
| 1 | 27.20 | 30.85 | +3.65 |
| 2 | 32.29 | 31.55 | −0.74 |
| 3 | 30.46 | 32.82 | +2.34 |
| 4 | 27.50 | 31.93 | +4.43 |
| 5 | 27.79 | 30.99 | +3.20 |
| 6 | 24.30 | 31.28 | +6.98 |
| 7 | 26.55 | 31.14 | +4.59 |
| 9 | 31.28 | 32.52 | +1.24 |
| 11 | 24.50 | 31.67 | +7.17 |
| 12 | 29.97 | 32.57 | +2.60 |
| 13 | 24.87 | 31.73 | +6.86 |
| 14 | 29.06 | 32.33 | +3.27 |
| 16 | 23.55 | 31.03 | +7.48 |
| 17 | 32.53 | 32.13 | −0.40 |
| 18 | 24.53 | 31.59 | +7.06 |
| 20 | 30.75 | 31.93 | +1.18 |
| 21 | 31.84 | 32.04 | +0.20 |
| Ave. | 28.18 | 31.77 | +3.59 |

Figure 3:
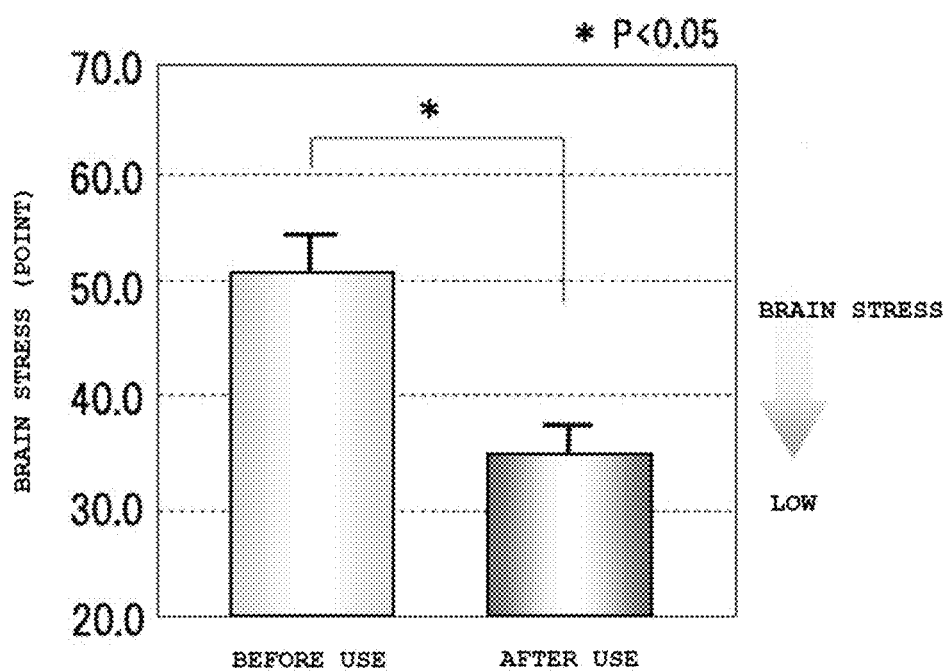
FIG. 3 illustrates a graph illustrating an average before and after the suctioning of hydrogen by the subject in brain stress evaluation.
Figure 4:
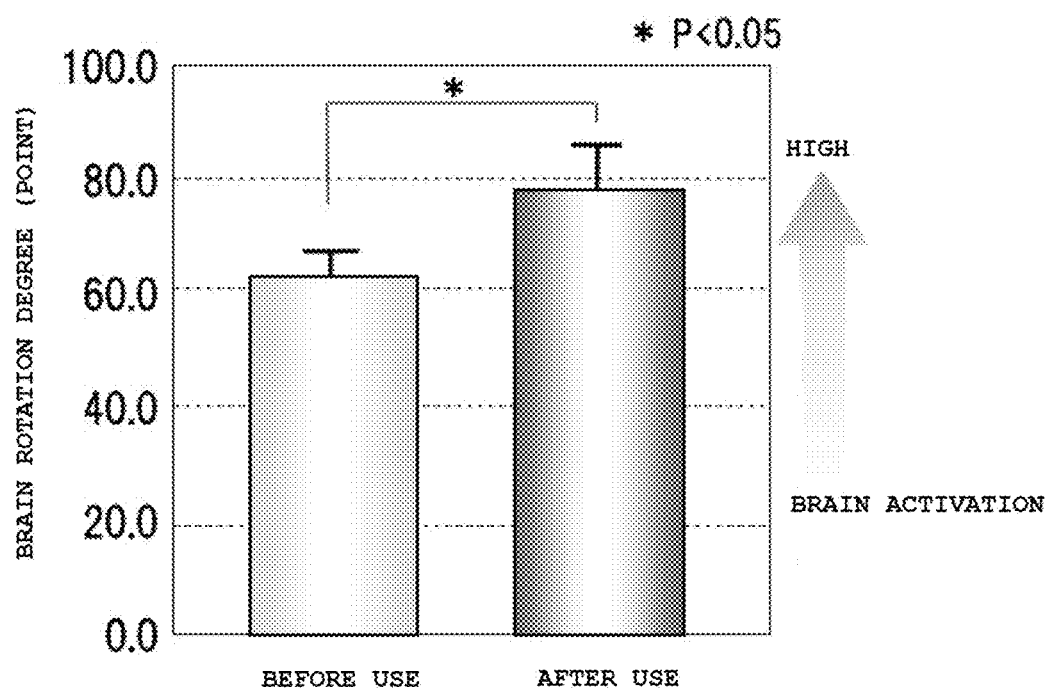
FIG. 4 illustrates a graph illustrating an average before and after the suctioning of hydrogen by the subject in a rotation degree evaluation of the brain.

The results (including brain age evaluation) of 2-1) Brain stress test and 2-2) Flicker measurement are as in the following Table 3, and FIG. 3 shows a graph illustrating an average of the 17 subjects in the brain stress evaluation converted into an evaluation in score from Table 3 before and after the suctioning of hydrogen, similarly to FIGS. 1 and 2. It was suggested from this Table 3 and FIG. 3 that the brain stress was significantly decreased by the hydrogen suctioning and the stress reduction effect. Moreover, FIG. 4 shows a graph illustrating an average of 17 subjects in the brain rotation degree evaluation which is converted to an evaluation in score from Table 3 before and after the hydrogen suctioning, similarly to FIGS. 1 to 3. It was suggested from this Table 3 and FIG. 4 that the brain rotation degree score was significantly raised by the hydrogen suctioning, and the brain function was activated.

TABLE 3

| Subject | Flicker value (average) | | | Brain age (years old) | | | Brain stress (%) | | |
|---|---|---|---|---|---|---|---|---|---|
| | Before | After | Difference | Before | After | Difference | Before | After | Difference |
| 1 | 44.7 | 45.3 | +0.7 | 22 | 20 | −2.0 | 30 | 68 | +38.0 |
| 2 | 41.7 | 41.3 | −0.3 | 46 | 44 | −2.0 | 51 | 26 | −25.0 |
| 3 | 35.7 | 35.0 | −0.7 | 29 | 30 | +1.0 | 39 | 11 | −28.0 |
| 4 | 47.3 | 51.3 | +4.0 | 19 | 31 | +12.0 | | 66 | +66.0 |
| 5 | 46.3 | 50.0 | +3.7 | 16 | 16 | ±0.0 | 58 | 56 | −2.0 |
| 6 | 41.0 | 41.3 | +0.3 | 26 | 23 | −3.0 | 45 | 97 | +52.0 |
| 7 | 49.0 | 50.0 | +1.0 | 25 | 24 | −1.0 | 79 | 27 | −52.0 |
| 9 | 46.0 | 49.7 | +3.7 | 17 | 16 | −1.0 | 38 | 37 | −1.0 |
| 11 | 43.0 | 43.0 | +0.0 | 21 | 34 | +13.0 | 49 | 37 | −12.0 |
| 12 | 41.7 | 40.0 | −1.7 | 28 | 29 | +1.0 | 37 | 23 | −14.0 |
| 13 | 47.0 | 45.0 | −2.0 | 45 | 32 | −13.0 | 31 | 22 | −9.0 |
| 14 | 39.7 | 46.7 | +7.0 | 28 | 26 | −2.0 | 9 | 15 | +6.0 |
| 16 | 45.33 | 41.7 | −3.7 | 43 | 25 | −18.0 | 58 | 28 | −30.0 |
| 17 | 42 | 39.7 | −2.3 | 34 | 29 | −5.0 | 37 | 38 | +1.0 |
| 18 | 38.3 | 38.3 | ±0.0 | 32 | 32 | ±0.0 | 14 | 37 | +23.0 |
| 20 | 45 | 45.7 | +0.7 | 29 | 26 | −3.0 | 58 | 94 | +36.0 |
| 21 | 39.3 | 39.7 | +0.3 | 18 | 29 | +11.0 | 44 | 16 | −28.0 |
| Ave. | 43.4 | 43.75 | +0.6 | 28.1 | 27.4 | −0.7 | 42.3 | 41.1 | +1.2 |

1 Flicker value (average)
2 Brain age (years old)
3 Brain stress (%)
4 Subject
5 Before
6 After
7 Difference The result of 2-3) Brain function measurement is as in the following Table 4, which is a result converted into an evaluation in score of a visual sense, an aural sense, finger tapping, grasping power, gravity balance, cognitive function (right-and-left cognitive function, short-term memory). The short-term memory and the right-and-left cognitive function should attract attention. FIG. 5 shows a graph illustrating an average of the 17 subjects before and after the hydrogen suctioning, similarly to FIGS. 1 to 4. The "remarkable improvement" in the short-term memory and the right-and-left cognitive function by the hydrogen suctioning was suggested from this Table 4 and FIG. 5.

TABLE 4

| Subject | Visual function | | | Aural function | | | Skin sensibility function | | | Finger motion function | | |
|---|---|---|---|---|---|---|---|---|---|---|---|---|
| | Before | After | Difference | Before | After | Difference | Before | After | Difference | Before | After | Difference |
| 1 | 6 | 6 | ±0 | 6 | 7 | +1 | 7 | 7 | ±0 | 4 | 7 | +3 |
| 2 | 2 | 5 | +3 | 6 | 6 | ±0 | 6 | 6 | ±0 | 3 | 3 | ±0 |
| 3 | 0 | 2 | +2 | 3 | 5 | +2 | 0 | 0 | ±0 | 1 | 2 | +1 |
| 4 | 0 | 1 | +1 | 3 | 4 | +1 | 4 | 4 | ±0 | 4 | 5 | +1 |
| 5 | 0 | 1 | +1 | 2 | 4 | ±2 | 2 | 2 | ±0 | 2 | 4 | +2 |
| 6 | 0 | 2 | +2 | 6 | 6 | ±0 | 6 | 6 | ±0 | 4 | 5 | +1 |
| 7 | 4 | 4 | ±0 | 6 | 6 | ±0 | 6 | 5 | −1 | 5 | 7 | +2 |
| 9 | 0 | 0 | ±0 | 0 | 0 | ±0 | 0 | 2 | +2 | 3 | 5 | +2 |
| 11 | 0 | 1 | +1 | 0 | 0 | ±0 | 0 | 0 | ±0 | 4 | 4 | ±0 |
| 12 | 3 | 3 | ±0 | 6 | 6 | ±0 | 6 | 6 | ±0 | 5 | 5 | ±0 |
| 13 | 2 | 3 | +1 | 5 | 6 | +1 | 6 | 4 | −2 | 3 | 1 | −2 |
| 14 | 1 | 1 | ±0 | 1 | 4 | +3 | 0 | 0 | ±0 | 1 | 5 | +4 |
| 16 | 1 | 3 | +2 | 6 | 6 | ±0 | 6 | 5 | −1 | 4 | 4 | ±0 |
| 17 | 3 | 4 | +1 | 6 | 6 | ±0 | 1 | 4 | +3 | 3 | 5 | +2 |
| 18 | 4 | 5 | +1 | 6 | 6 | ±0 | 6 | 6 | ±0 | 6 | 7 | +1 |
| 20 | 4 | 4 | ±0 | 6 | 6 | ±0 | 6 | 6 | +1 | 10 | 8 | −2 |
| 21 | 0 | 1 | +1 | 3 | 2 | −3 | 3 | 4 | +1 | 3 | 3 | ±0 |
| Ave. | 1.8 | 2.7 | +0.9 | 4.2 | 4.7 | +0.5 | 3.8 | 3.9 | +0.2 | 3.8 | 4.7 | +0.9 |

| Subject | Attitude function | | | Knee motion function | | | Right-and-left cognitive function | | | Short-term memory | | |
|---|---|---|---|---|---|---|---|---|---|---|---|---|
| | Before | After | Difference | Before | After | Difference | Before | After | Difference | Before | After | Difference |
| 1 | 10 | 10 | ±0 | ±0 | 0 | ±0 | 0 | 8 | +8 | 3 | 9 | +6 |
| 2 | 6 | 10 | +4 | 10 | 8 | −2 | 0 | 9 | +9 | 0 | 8 | +8 |
| 3 | 0 | 0 | ±0 | 9 | 6 | −3 | 0 | 8 | +8 | 0 | 9 | +9 |
| 4 | 10 | 10 | ±0 | 0 | 0 | ±0 | 0 | 7 | +7 | 0 | 6 | +6 |
| 5 | 10 | 10 | ±0 | 0 | 5 | +5 | 1 | 7 | +6 | 0 | 7 | +7 |
| 6 | 10 | 10 | ±0 | 0 | 10 | +10 | 0 | 9 | +9 | 0 | 8 | +8 |
| 7 | 10 | 10 | ±0 | 10 | 10 | ±0 | 0 | 7 | +7 | 1 | 6 | +5 |
| 9 | 7 | 10 | +3 | 0 | 0 | ±0 | 0 | 6 | +6 | 0 | 7 | +7 |

TABLE 4-continued

| | | | | | | | | | | | | |
|---|---|---|---|---|---|---|---|---|---|---|---|---|
| 11 | 0 | 0 | ±0 | 10 | 10 | ±0 | 1 | 6 | +5 | 0 | 5 | +5 |
| 12 | 10 | 7 | −3 | 10 | 10 | ±0 | 3 | 8 | +5 | 0 | 9 | +9 |
| 13 | 10 | 0 | −10 | 8 | 10 | +2 | 0 | 9 | +9 | 6 | 9 | +3 |
| 14 | 10 | 10 | ±0 | 7 | 0 | −7 | 0 | 9 | +9 | 0 | 9 | +9 |
| 16 | 10 | 10 | ±0 | 0 | 0 | ±0 | 0 | 7 | +7 | 0 | 8 | +8 |
| 17 | 10 | 10 | ±0 | 0 | 0 | ±0 | 0 | 8 | +8 | 0 | 8 | +8 |
| 18 | 10 | 7 | −3 | 1 | 9 | +8 | 0 | 8 | +8 | 0 | 9 | +9 |
| 20 | 10 | 10 | ±0 | 0 | 0 | ±0 | 0 | 8 | +8 | 0 | 8 | +8 |
| 21 | 10 | 10 | ±0 | 10 | 10 | ±0 | 5 | 7 | +2 | 0 | 6 | +6 |
| Ave. | 8.4 | 7.9 | −0.5 | 4.4 | 5.2 | +0.8 | 0.6 | 7.7 | +7.1 | 0.6 | 7.7 | +7.1 |

Figure 6:
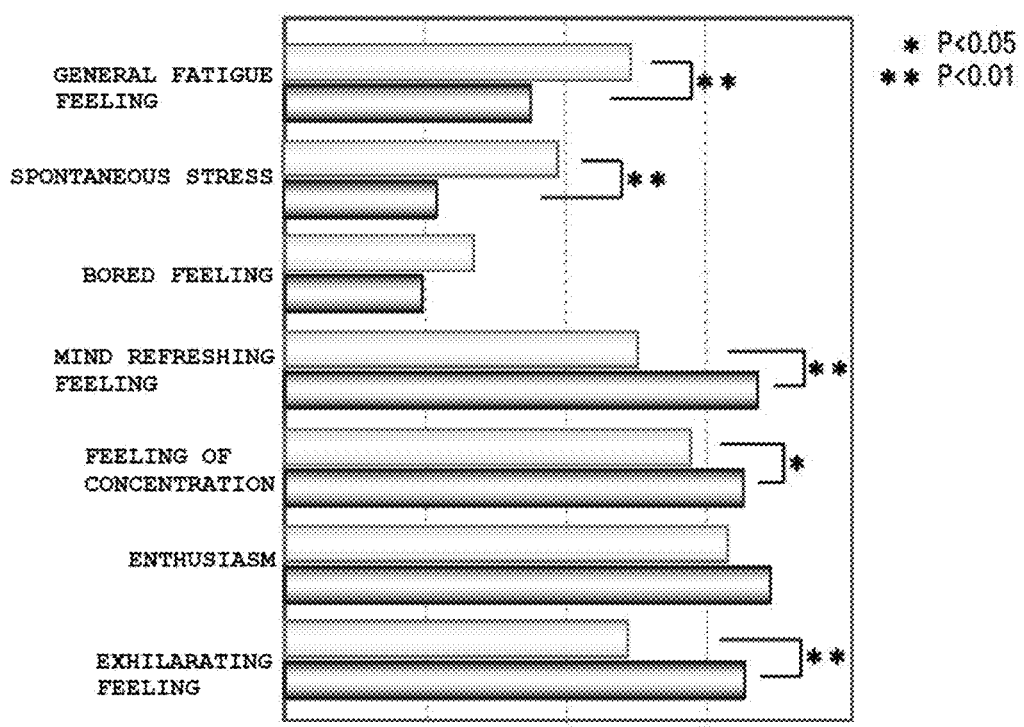
FIG. 6 illustrates a graph illustrating an average before and after the suctioning of hydrogen by the subject in a result of planar emotional state scale.

1 Visual function
2 Aural function
3 Skin sensibility function
4 Finger motion function
5 Attitude function
6 Knee motion function
7 Right-and-left cognitive function
8 Short-term memory
9 Subject
10 Before
11 After
12 Difference The result of 2-4) Multilateral emotional state scale is shown in FIG. 6. FIG. 6 also shows a graph illustrating an average of the 17 subjects before and after the hydrogen suctioning, similarly to FIGS. 1 to 5. This result showed that the fatigue feeling and spontaneous stress decreased by the hydrogen suctioning, while feelings of refreshing, concentration, and exhilarating were significantly raised.

Subsequently, a typical embodiment of the electrolytic hydrogen gas suction tool 100 as a hydrogen generating device recommended for executing the bioactivation method for enhancing the neural activity and/or blood circulation activity of a living body of the present invention will be described in detail by referring to FIGS. 7 to 10, but it is needless to say that the present invention is not limited to the illustration. Moreover, since each drawing is for conceptually describing the present invention, dimensions, ratios, or numbers may be exaggerated or simplified in notation for facilitation of understanding as necessary in some cases. Furthermore, the same reference numerals are given to the same or corresponding portions, and duplicated description may be omitted in the following description in some cases.

Figure 7:
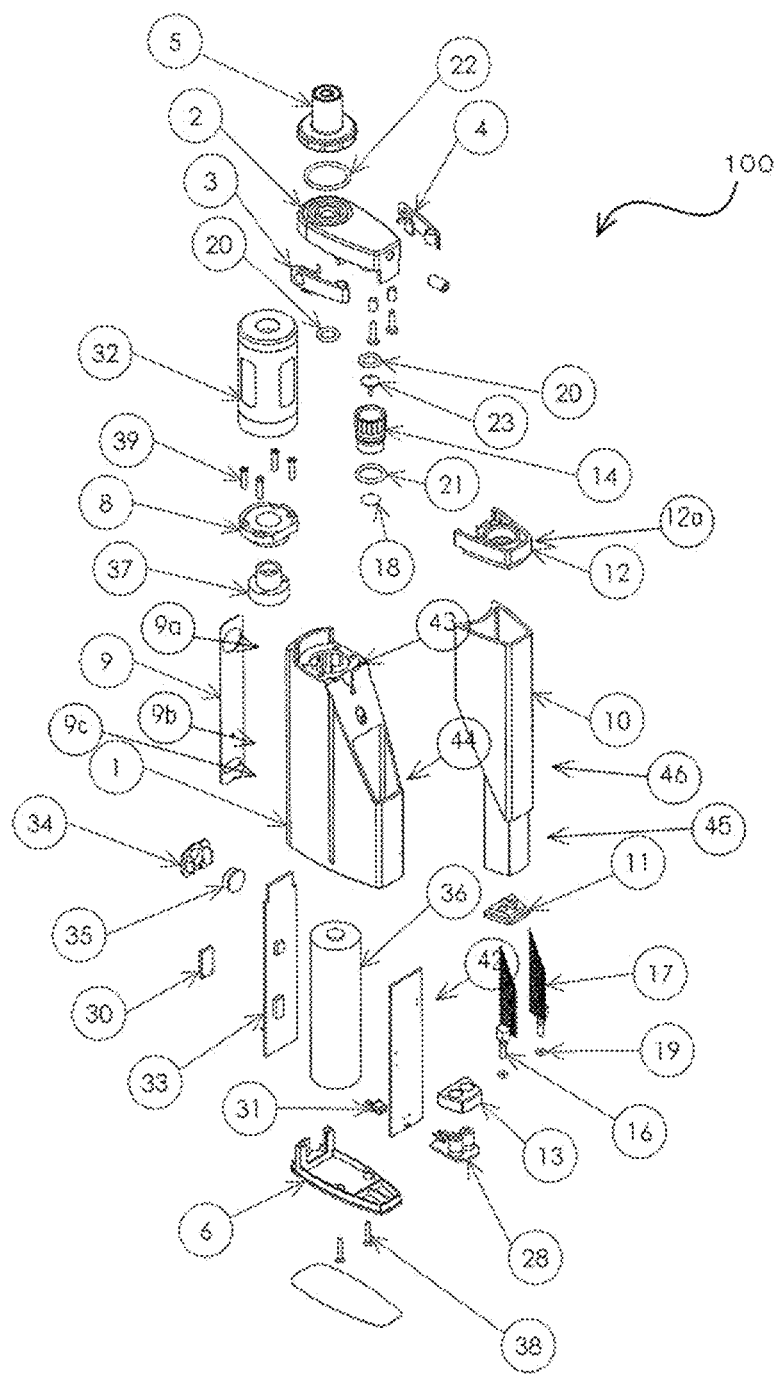
FIG. 7 is an assembling/disassembling view exemplifying each member of an electrolytic hydrogen gas suction tool of the present invention.
Figure 8:
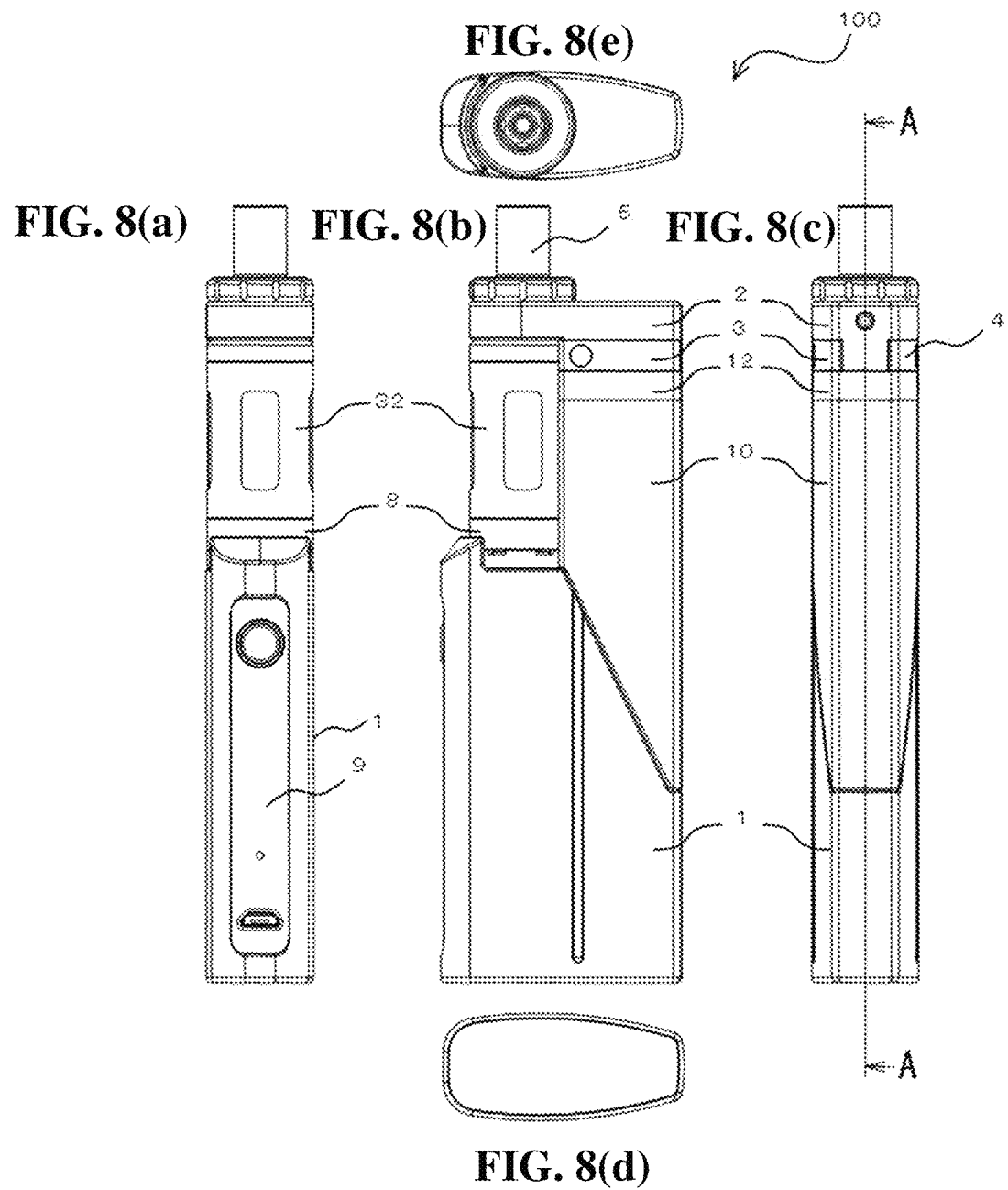

FIG. 7 is an assembling/disassembling view exemplifying each member of the electrolytic hydrogen gas suction tool 100 of the present invention. Moreover, FIGS. 8 are views of the electrolytic hydrogen gas suction tool 100 in FIG. 7 when seen from each direction, in which FIG. 8(a) is a left side view, FIG. 8(b) is a front view, FIG. 8(c) is a right side view, FIG. 8(d) is a bottom view, and FIG. 8(e) is a top view. In this description, an up-and-down direction and a longitudinal direction refer to the up-and-down direction on the drawing of FIG. 8(b) and a longitudinal direction of the drawing, and a width direction, a lateral direction, and a side portion side refer to the right-and-left direction of the drawing, the lateral direction of the drawing, and the right-and-left side portion side of the drawing in FIG. 8(b).

Figure 9:
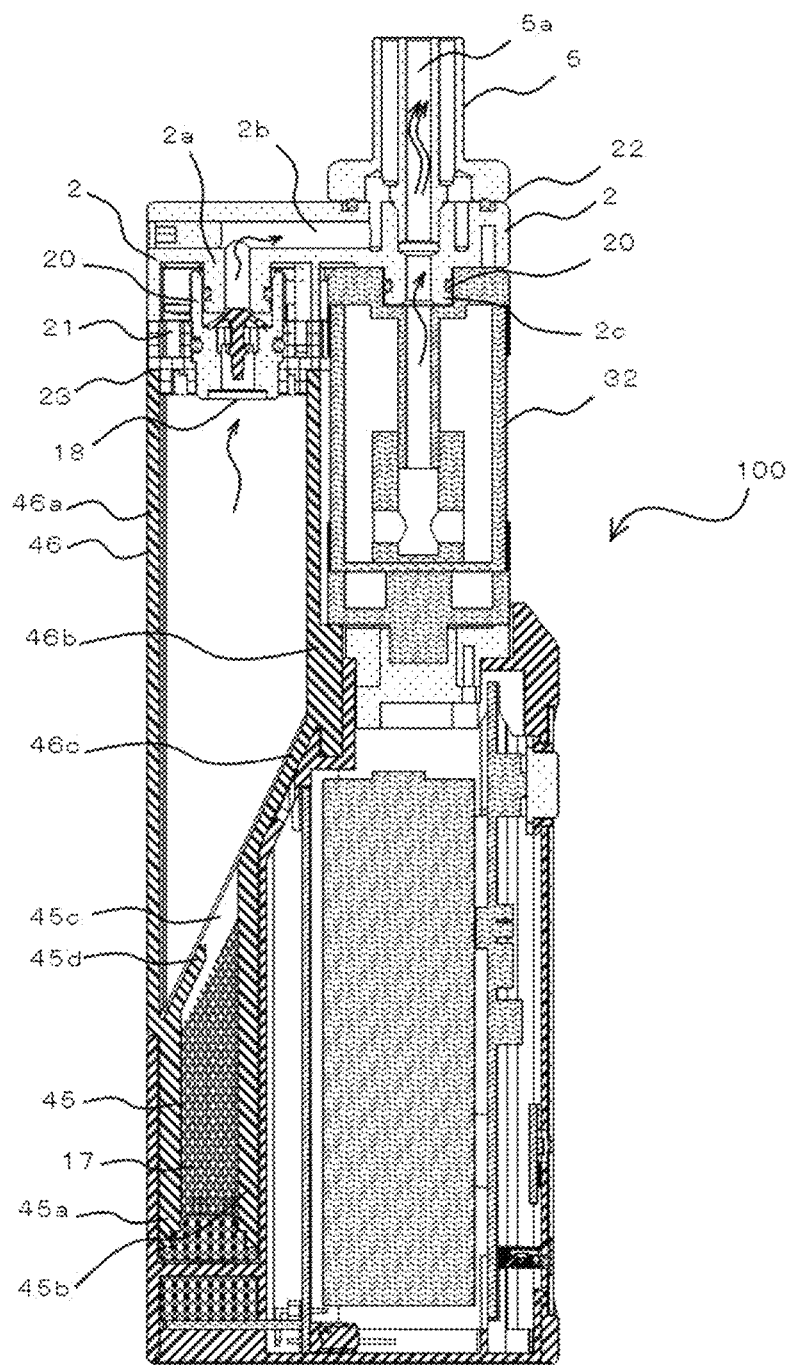
FIG. 9 illustrates a sectional view of the electrolytic hydrogen gas suction tool in FIGS. 7 to 8 along a line A-A in FIG. 8(c).
Figures 10A, 10B:
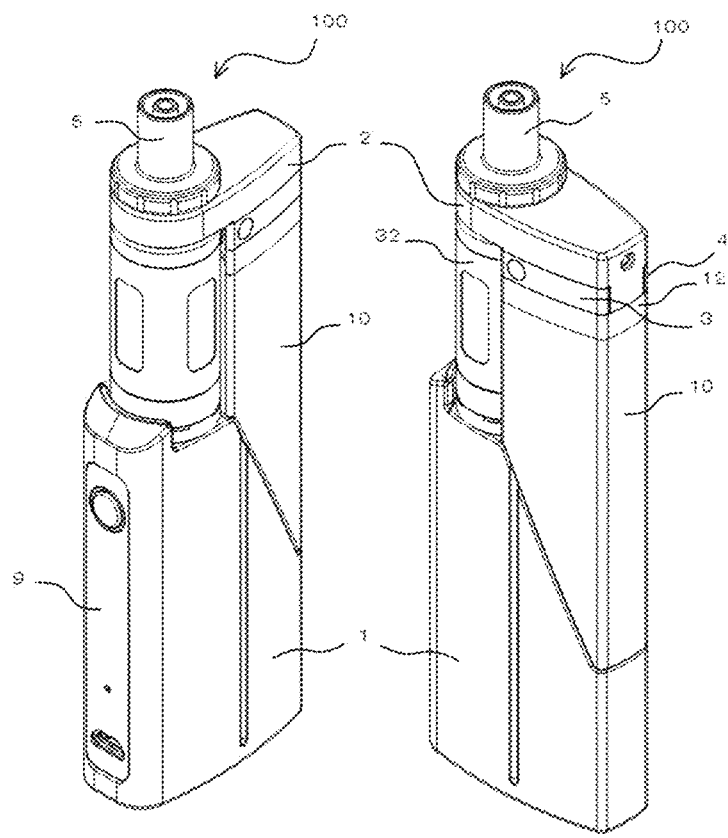
FIG. 10(a) illustrates a perspective view of the electrolytic hydrogen gas suction tool in FIGS. 7 to 9 when seen from above on lower left of the drawing in FIG. 8(b) and FIG. 10(b) from above on lower right of the drawing in FIG. 8(b).

Moreover, FIG. 9 illustrates a sectional view of the electrolytic hydrogen gas suction tool 100 in FIGS. 7 to 8 along a line A-A in FIG. 8(c). Furthermore, FIG. 10(a) is a perspective view of the electrolytic hydrogen gas suction tool 100 in FIGS. 7 to 9 when seen from above on lower left of the drawing in FIG. 8(b) and FIG. 10(b) from above on lower right of the drawing in FIG. 8(b).

Hereinafter, the electrolytic hydrogen gas suction tool 100 will be described by referring mainly to the assembling/disassembling view in FIG. 7 and will be referred to the other drawings for convenience of the description.

As described above, FIG. 7 illustrates a configuration example of each member of this hydrogen gas suction tool 100. A body cover 1 is a case made of a resin in which a battery receiving portion 43 opened upward and into which an entire battery 36 is inserted/stored in the vertical direction from the opening and an electrolysis tank receiving portion 44 having a shape arranged in parallel in the vertical direction with the battery receiving portion 43 and into which a reduced diameter portion 45 on a lower part of the electrolysis tank 10 can be inserted and fitted from above are provided. A battery 36 used here is preferably a charging-type lithium battery.

The body cover 1 has a shape which is longer on the battery receiving portion 43 side, and the electrolysis tank receiving portion 44 side is cut out so that the upper part is inclined to the side. With respect to the battery 36, a bottom part of the body cover 1 can open/close the bottom part of the battery receiving portion 43 with a body bottom cover 6 as a lid member and closes the bottom part of the battery receiving portion 43 with the body bottom cover 6 after the battery 36 is inserted from the bottom part during assembling. The body bottom cover 6 is closed by a cross recessed screw 38. Moreover, in the body cover 1, spaces in which two control substrates (electronic substrates) 33 and 42 are disposed so as to sandwich the battery 36 in the vertical direction on the both side portion sides of the battery receiving portion 43 are provided, and the control substrate 33 on the side surface side of the body cover 1 is a main control substrate and controls power supply from the battery 36 with the control substrate 42 on the electrolysis tank 10 side performing power supply to an aromatic heater member 32 (aroma generating device) and a mesh electrode 17 (electrode plate).

A decorative laminated sheet 9 is attached to the side surface of the body cover 1 along the longitudinal side surface, and a button hole 9a through which an operation button 35 to the control substrate 33 is seen, a hole 9b for LED for light irradiation from an LED substrate 30, and a hole 9c for charging connector for connecting a connector for charging the battery 36 from an external power source are provided on the decorative laminated sheet 9 in this order from the top.

By pressing on the operation button 35 three times, a power supply signal is transmitted in the control substrate 33 to the control substrate 42, and power of the battery 36 is supplied for a predetermined time to a pair of the mesh electrodes (electrode plates) 17 through a housing 31 for substrate connector and a crimping substrate 28. When the power is supplied to the mesh electrode 17, the power supply signal is transmitted in the control substrate 33 to the LED substrate 30, and the LED substrate 30 causes the LED to emit light. As a result, the user can visually recognize a hydrogen gas generation state by the hole 9b for LED. Pressing on the operation button 35 three times was made a condition for the power supply to the mesh electrode 17 as a safety condition to avoid unintentional button operation and power supply when the user moves with this hydrogen gas suction tool 100 put in a pocket or the like.

The mesh electrodes 17 are disposed upward in a pair of two electrodes in parallel longitudinally, each forming positive/negative electrodes and corresponding to power from the positive/negative poles of the battery 36. Moreover, an upper end of the mesh electrode 17 has a shape cut out diagonally so as to correspond to a boundary line between the reduced diameter portion 45 and a water storage body portion 46 of the electrolysis tank 10. To a lower end of the mesh electrode 17, a rod-shaped titanium electrode 16 is connected so as to stand upright on a terminal substrate 28 and can be electrically connected thereto. In order to shield the mesh electrode substrate 17 and the terminal substrate 28 from water in a state where the mesh electrode 17 stands upright, a packing 13 (made of a resin such as silicone) to be attached on the terminal substrate 28 and an O-ring (made of resin such as silicone: hereinafter the same applies to the O-ring) attached around the titanium electrode 16 are provided.

The electrolysis tank 10 is a container for storing water, the reduced diameter portion 45 and the water storage body portion 46 are integrally formed in order from below, and they are connected to each other therein fluidically. The water storage body portion 46 is opened upward so that water can be poured in and is half-closed by attaching an electrolysis tank lid 12. The electrolysis tank lid 12 penetrates vertically, and a penetrating opening 12a for receiving an umbrella valve 23, a screw cap 14 and the like is provided. In the water storage body portion 46, an outer side portion 46a forms a side wall substantially flat in the lateral direction from an upper end to a lower end as illustrated in FIG. 9 and is connected as it is to the upper end of the reduced diameter portion 45, and an inner side portion 46b on the body cover 1 side has a bottom portion 46c formed in parallel with the outer side portion 46a from the upper end to a lower center position and bending from the lower center position and inclined. The bottom portion 46c extends to a middle position in the lateral direction and is connected to the upper end of the reduced diameter portion 45.

Moreover, the reduced diameter portion 45 is thinner than the water storage body portion 46 as described above, and the upper end of the outer side portion 46a on the side wall side is continuously connected as it is to the lower end of the outer side portion 46a of the water storage body portion 46 and extends to the lower end as illustrated in FIG. 9, and the upper end of the inner side portion 46b on the body cover 1 side is bent downward and connected at a position of a distal end (edge part) of the bottom portion 46c of the water storage body portion 46 and extends to the lower end in parallel with the inner side portion 46b.

Moreover, at a connection position between the lower end of the outer side portion 46a of the water storage body portion 46 and the upper end of the outer side portion 46a of the reduced diameter portion 45, a partition plate 45d inclined substantially the same as the bottom portion 46c of the water storage body portion 46 and extending to the opening 45c is provided. This partition plate 45d extends inside the whole region in a perpendicular direction on the drawing in FIG. 9. Therefore, even if an aqueous solution collecting in the electrolysis tank 10 is electrolyzed and a water storage amount decreases, the water is stored substantially in the whole region inside the reduced diameter portion 45 at all times. More specifically, when the water storage amount decreases, and an air layer is formed partially in the electrolysis tank 10, since the reduced diameter portion 45 is thinner than the water storage body portion 46, water is fully filled in the reduced diameter portion 45 in a normal standing state and thus an air layer is not generated as long as the water storage amount doesn't decrease too much.

Moreover, when the water storage amount decreases to some degree, too, an air layer can be generated in the reduced diameter portion 45 if this hydrogen gas suction tool 100 is inclined or placed horizontally, but in the case of this electrolysis tank 10, water is fully filled in the reduced diameter portion 45 even in this case. More specifically, in the case of inclination in the left direction on the drawing in FIG. 9, for example, the bottom portion 46c becomes a baffle plate, and an air layer is formed on the inner side portion 46b side in the water storage body portion 46. On the other hand, in the case of inclination in the right direction on the drawing in FIG. 9, the partition plate 45d becomes the baffle plate, and the air layer is formed only on the outer side portion 46a side of the water storage body portion 46. Therefore, the entire mesh electrode 17 disposed in the reduced diameter portion 45 is in contact with water at all times, and even if the user is suctioning sideways, the amount of hydrogen generated can be always ensured.

An upper end edge of the mesh electrode 17 is formed by being cut out diagonally so that the electrode is soaked in water in the reduced diameter portion 45 without a gap by following the shapes of the reduced diameter portion 45 and the opening 45c. Returning to FIG. 7 again, the lower end of the electrolysis tank 10 is closed by an electrolysis tank bottom 11, but the electrolysis tank bottom 11 has a pair of through holes into which the mesh electrodes 17 are inserted provided, and when the reduced diameter portion 45 of the electrolysis tank 10 is inserted into the electrolysis tank receiving portion 44 of the body cover body 1, the mesh electrode 17 passes through the through hole of the electrolysis tank bottom 11 and is positioned in the reduced diameter portion 45.

The umbrella valve 23 and the like attached to the penetrating opening 12a of the electrolysis tank lid 12 on the upper end of the electrolysis tank 10 will be described. To the penetrating opening 12a, the screw cap 14 having an opening on an upper part and penetrating vertically is attached, and at that time, a vent filter 18 is interposed between a hole in the bottom part of the screw cap 14 and the bottom part of the penetrating opening 12a, and the O-ring 21 is inserted into the periphery on a lower part of the screw cap 14. The vent filter 18 is a micro hole and has a function of preventing water/dusts while adjusting an internal pressure in the opening of the screw cap 14. Moreover, the O-ring 21 shields a space between an outer peripheral wall of the opening in the screw cap 14 and an inner peripheral wall of the penetrating opening 12a from water.

Moreover, the umbrella valve 23 (made of a material having flexibility such as silicone) operating in the up-anddown direction is attached in the opening of the screw cap 14, and when the user suctions through the nozzle 5 (which will be described later), and a negative pressure acts upward, the umbrella valve 23 is raised/operated and is fluidically connected to the inside of the electrolysis tank 10 through a through hole in the bottom part of the screw cap 14 and the penetrating opening 12a of the electrolysis tank lid 12. Therefore, when the user suctions through the nozzle 5, the hydrogen gas raised and collecting in the electrolysis tank 10 is emitted to an outside. On the contrary, if the user stops suctioning, and a state in which the negative pressure does not act is brought about, the umbrella valve 23 is lowered/operated, the through hole in the bottom part of the screw cap 14 is closed, and the emission of the hydrogen gas in the electrolysis tank 10 is closed.

To the electrolysis tank lid 12 to which the screw cap 14 and the umbrella valve 23 are attached, a mixer 2 is attached from above. The mixer 2 has a cylindrical member 2a extending downward as illustrated in FIG. 9, and by inserting a lower end of the cylindrical member 2a into the opening of the screw cap 14, the cylindrical member 2a forms a channel for guiding the hydrogen gas from the umbrella valve 23 upward. The O-ring 21 is provided around the outer peripheral wall of this cylindrical member 2a and seals a gap from the inner wall of the opening in the screw cap 14.

Fixation of the mixer 2 and the electrolysis tank lid 12 is accomplished by attaching lock buttons 3 and 4. The lock buttons 3 and 4 are sandwiched and snap-fastened in a front-and-rear direction (the perpendicular direction on the drawing in FIG. 9) at a gap position in the up-and-down direction between the mixer 2 and the electrolysis tank lid 12, respectively. Moreover, the mixer 2 has a channel 2b provided toward the nozzle 5 direction in an upper part thereof as illustrated in FIG. 9. This channel 2b is connected to the channel formed in the cylindrical member 2a and guides the hydrogen gas as indicated by an arrow in FIG. 9.

Subsequently, though not desired as the electrolytic hydrogen gas suction tool 100 as the hydrogen generating device for executing the bioactivation method for enhancing the neural activity and/or the blood circulation activity of a living body of the present invention, an aromatic heater member 32 for generating an aromatic air may be provided in order to satisfy preference when the user use is in a daily life.

First, a contact terminal 37 of the battery 36 is inserted into the upper-end opening of the battery receiving portion 43 of the body cover 1. The contact terminal 37 is formed by connecting a bottom part of a large-diameter cylinder and an upper part of a small-diameter cylinder, the bottom part is inserted into the opening in the upper end of the battery receiving portion 43, and power from the battery 36 is supplied to the aromatic heater member 32. The contact terminal 37 is fastened to a joint 8 from above by a cross recessed flat head screw 39. The joint 8 is formed by connecting the bottom part and the upper part having a large diameter and a substantially disk shape of the small-diameter cylinder, and the upper part of the contact terminal 37 and the bottom part of the joint 8 are fitted in a nested state.

The aromatic heater member 32 is placed on an upper surface of a joint 8, and when the mixer 2 described above is to be attached, it is sandwiched by the joint 8 and the mixer 2 and is fixed to the body cover 1. The aromatic heater member 32 is a general-purpose device, and when power is supplied, an air with aroma is generated therein and is emitted upward. Moreover, a cylindrical member 2c extending downward in parallel with the cylindrical member 2a described above is provided on the mixer 2, and an upper end of the aromatic heater member 32 is connected to this cylindrical member 2c. Therefore, the air with aroma emitted from the aromatic heater member 32 passes through the cylindrical member 2c as indicated by the arrow in FIG. 9, merges with the hydrogen gas flowing through the channel 2b through the cylindrical member 2a, flows into the nozzle 5 and is emitted into the mouth of the user.

The nozzle 5 has a structure in which a large diameter and substantially disk-shaped member on the bottom part and the cylindrical member on the upper part are integrally connected, and the bottom part is attached onto the opening in the top surface fluidically connected to the cylindrical member 2c of the aromatic heater member 32 in the mixer 2. As a result, the hydrogen gas from the channel 2b and/or the air with aroma from the cylindrical member 2c are emitted from inside the nozzle 5 to the outside of the upper end. The O-ring 22 is disposed on the connection portion between the bottom part of the nozzle 5 and the mixer 2 and sealed.

Moreover, the aromatic heater member 32 controls power supply from the battery 36 by the control substrate 33. As described above, the power to the mesh electrode substrate 17 is supplied for the predetermined time by pressing on the button 35 attached to the body cover 1 three times. On the other hand, by holding down the button, the contact terminal 37 is connected under a condition that the power supply signal to the mesh electrode 17 is not transmitted in the control substrate 33, and the power from the battery 36 is supplied to the aromatic heater member 32 for the predetermined time.

Therefore, by pressing on the button 35 three times, when the user suctions through the nozzle 5, the hydrogen gas is emitted from the nozzle 5, and hydrogen gas suctioning can be enjoyed for the predetermined time (while the LED substrate 30 emits light), and by holding down the button 35 while the hydrogen gas is emitted, the hydrogen gas with aroma can be enjoyed.

The bioactivation method for enhancing the neural activity and/or the blood circulation activity of a living body of the present invention and the electrolytic hydrogen gas suction tool 100 as the hydrogen generating device recommended for executing this method have been described by exemplifying the embodiment thereof, but the present invention is not limited to them, and those skilled in the art can understand that other variations and improvements can be obtained within a range not departing from the spirit or teaching of the description in claims, the description and the like.

INDUSTRIAL APPLICABILITY

According to the bioactivation method for enhancing the neural activity and/or the blood circulation activity of a living body of the present invention, a favorable psychological/physiological effect can be generated quickly by suctioning the hydrogen gas at the predetermined concentration continuously for the predetermined time. It is particularly remarkable in brain activation (right-and-left cognitive function, short-time memory).

Moreover, according to the hydrogen generating device used for executing the bioactivation method for enhancing the neural activity and/or the blood circulation activity of a living body, since this is a charging type so that the user can carry it freely, the battery is small-sized and inexpensive but a space for storing the battery and water shielding between the electrolysis tank and the battery are ensured and moreover, a sufficient amount of hydrogen generated can be ensured even if it is tilted in a state where the water in the electrolysis tank has decreased, the user can suction hydrogen so as to obtain the aforementioned psychological/physiological effects easily and in a short time, not depending on the place as long as the user wishes.

REFERENCE SIGNS LIST 100 electrolytic hydrogen gas suction tool
1 body cover
2 mixer
13 hydrogen passing member
13a film material (breathable impermeable material)
14 ample portion
15 lid member
16 metal material
17 container body portion
18 aqueous solution
19 closing member
20 hydrogen
22 non-reaction portion
24 metal particle layer
40 projecting shaped portion
41 thin portion
100, 200 hydrogen gas suction tool
102 suction tool body portion
104 suctioning sheath portion
105 cap member
106, 206 connection portion
108, 208 mouth member
110, 210 film packing
112 control valve
113, 213 window
114 adjustment port
116 cartridge
117, 217 gap
118 O-ring

The invention claimed is:

1. A bioactivation method for enhancing a neural activity and/or a blood circulation activity of a living body by using a hydrogen generating device, the method comprising: suctioning a gas mixture containing hydrogen and oxygen at predetermined concentrations by spontaneously and continuously breathing for a predetermined time, wherein the hydrogen generating device comprising:

a body cover member including a battery, a control substrate for controlling power supply from the battery, and a pair of positive and negative electrodes electrically conducted with or shut down from a positive electrode and a negative electrode of the battery by the control substrate;

an electrolysis tank for storing water and detachably mounted on the body cover member, wherein the pair of positive and negative electrodes is disposed in the electrolysis tank;

a nozzle portion having a through hole;

a mixing portion fluidically connecting the nozzle portion and an end portion of the electrolysis tank and having a channel for delivering the hydrogen from the electrolysis tank to the nozzle portion by sucking; and a heater member disposed on top of the battery and configured to generate air, wherein the air generated by the heater member flows to the through hole of the nozzle portion and merges with the hydrogen delivered through the channel.

2. The bioactivation method according to claim 1, further comprising breathing the gas mixture emitted from the hydrogen generating device and mixed with an ambient air, wherein a same degree of the oxygen concentration as that of the ambient air is orally suctioned.

3. The bioactivation method according to claim 2, wherein the step of suctioning is performed for 10 minutes.

4. A hydrogen generating device for for enhancing a neural activity and/or a blood circulation activity of a living body, comprising:

a body cover member including a battery, a control substrate for controlling power supply from the battery, and a pair of positive and negative electrodes electrically conducted with or shut down from a positive electrode and a negative electrode of the battery by the control substrate;

an electrolysis tank for storing water and detachably mounted on the body cover member, wherein the pair of positive and negative electrodes is disposed in the electrolysis tank;

a nozzle portion having a through hole; and a mixing portion fluidically connecting the nozzle portion and an end portion of the electrolysis tank and having a channel for delivering the hydrogen from the electrolysis tank to the nozzle portion by sucking; and a heater member disposed on top of the battery and configured to generate air, wherein the air generated by the heater member flows to the through hole of the nozzle portion and merges with the hydrogen delivered through the channel.

\* \* \* \* \*